United States Patent [19]

Lever et al.

[11] Patent Number: 5,342,490
[45] Date of Patent: Aug. 30, 1994

[54] ELECTROLYTIC DETECTION OF SULFUR

[75] Inventors: Alfred B. P. Lever, 4700 Keele St., North York, Canada, M3J 1P3; Yu-Hong Tse, North York, Canada; Pavel Janda, Prague, Czechoslovakia

[73] Assignee: Alfred B. P. Lever, Ontario, Canada

[21] Appl. No.: 896,320

[22] Filed: Jun. 10, 1992

[51] Int. Cl.$^5$ ............................................. G01N 27/333
[52] U.S. Cl. ...................... 204/153.19; 204/415; 204/416; 204/418
[58] Field of Search ............... 204/153.19, 403, 415, 204/416, 418, 419

[56] References Cited

U.S. PATENT DOCUMENTS

| | | | |
|---|---|---|---|
| 3,915,831 | 10/1975 | Riseman et al. | 204/153.19 |
| 4,379,041 | 4/1983 | Petranek et al. | 204/418 |
| 4,957,615 | 9/1990 | Ushizawa et al. | 204/431 |
| 5,132,001 | 7/1992 | Bakos et al. | 204/418 |

Primary Examiner—T. Tung
Attorney, Agent, or Firm—Darby & Darby

[57] ABSTRACT

A macrocyclic compound coated electrode may be used advantageously to detect and measure the concentration of sulfide in aqueous samples. The electrode is substantially unaffected by other interfering species which may be present in the aqueous sample. Use of the electrode provides for fast, accurate, on-line monitoring of sulfide concentration in aqueous effluents from, inter alia, pulp and paper plants, and oil and gas refineries.

19 Claims, 13 Drawing Sheets a - 25 mV/s
b - 50 mV/s
c - 100 mV/s
d - 150 mV/s
[Co(Tmtppa)] = $10^{-4}$ M

ELECTROLYTIC DETECTION OF SULFUR

BACKGROUND OF THE INVENTION

1. FIELD OF THE INVENTION

In one of its aspects, the present invention relates to a sulfur determination electrode. In another of its aspects, the present invention relates to the use of such an electrode in the electrolytic detection of sulfur in a sample containing oxidizable sulfur. In yet another of its aspects, the present invention relates to a process for manufacturing a sulfur detection electrode.

2. DESCRIPTION OF THE PRIOR ART

As concern for our environment grows, the governmental agencies of many countries are imposing restrictions and regulations concerning the disposal of chemicals and contaminants into the environment. With the passage of time these restrictions and regulations are becoming much more rigid in terms of the quantity of chemicals and contaminants which may be released into the environment. In part, this is due to discoveries relating to the extent to which these chemicals and contaminants affect the environment. Accordingly, the ability to detect and monitor these chemicals and contaminants is becoming increasingly necessary in order to control release thereof in a manner which complies with the governmental restrictions and regulations.

Sulfur-containing compounds are one group of compounds which have been found to be particularly detrimental to the environment. Typically, such compounds comprise and/or release oxidizable sulfur such as sulfide ion (e.g. $HS^-$, $S^{2-}$ and the like) and mercaptans (RSH). Thus, when these sulfur-containing compounds are released into the environment, sulfur is also released directly or indirectly. Sulfur-containing compounds are commonly found in the waste water effluent from pulp and paper plants, as well as from oil and gas refineries.

Heretofore, various methods have been employed to detect the presence and concentration of sulfur such as sulfide ion in aqueous samples.

One method involves the use of wet titration for measurement of the sulfide ion concentration. Once this concentration is determined, the concentration of the actual sulfur-containing compound may be determined. Unfortunately, the wet titration method is neither rapid nor efficient to serve the purposes of industry which require the ability to make multiple on-line measurements in a rapid fashion.

Another method for measurement of sulfide ion concentration involves utilizing ion chromatography coupled with electrochemical detection. See, for example, Anal. Chem., 54(3), 582-5 (Bond et al). The requirement of utilizing two analytical techniques renders this method cumbersome and, in some cases, lacking in precision and accuracy.

Yet another method for measurement of sulfide ion concentration involves utilizing a potentiometric method. See, for example, any one of Anal. Chem., 40(7), 1055 (1968) [Hseu et al], Anal. Chim. Acta, 51, 231 (1970) [Mascini et al] and Anal. Lttrs., 1(13), 825 (1968) [Light et al].

Yet another method for measurement of sulfide ion concentration utilizes a sulfide ion-selective membrane electrode obtained by incorporating silver sulfide into a silver silicon rubber matrix. See, for example, Anal. Chem., 39 (13) 28A (1967) [Pungor]. This method makes use of a sulfide-based ion-selective electrode (also known as an Orion electrode) to determine sulfide ion concentration in an aqueous solution. The detection of sulfide using this method is indirect for most applications insofar as the sulfide must be initially reacted with silver or lead to form silver or lead sulfide, each demonstrating low solubility. Thus, excess sulfide ion remaining in solution may then be detected and measured using the Orion electrode. In some cases, the Orion electrode may be used to make direct measurements of sulfide if the pH of the aqueous sample is buffered (or otherwise adjusted) to a value of 12. Thus, the method is relatively cumbersome and inefficient since in the indirect mode additional cost (for silver and lead chemicals), time and potential experimental error are incurred over and above the underlying electrochemical technique. Further, in the direct mode, additional cost (buffering agent) and time are incurred over and above the underlying electrochemical technique. Moreover, the Orion electrode is sensitive to a range of contaminants that may also be present in the aqueous sample and thus, it is important to know, at least qualitatively, the composition of the aqueous sample.

A Cu-O-loaded element for hydrogen sulfide ($H_2S$) detection has recently been reported in Chem. Lttrs., 575 (1991) [Maekawa et al]. However, there is no indication that this method is useful in the determination of the concentration (i.e. quantitative determination) of sulfide ion in an aqueous solution.

In light of the foregoing, there still exists a need for an electrode which allows for rapid, precise and accurate determination of sulfur from samples containing oxidizable sulfur, such as (i) aqueous samples comprising sulfide ion, and (ii) other sulphur containing compounds such as mercaptans.

SUMMARY OF THE INVENTION

It is an object of the present invention to provide a novel process for determining the concentration of sulfur in an aqueous sample containing oxidizable sulfur.

It is another object of the present invention to provide a novel apparatus for determining the concentration of sulfur in an aqueous sample containing oxidizable sulfur.

It is yet another object of the present invention to provide a novel process for manufacturing a sulfur determination electrode.

It is yet another object of the present invention to provide a novel sulfur determination electrode.

Accordingly, in one of its aspects, the present invention provides a process for determining the concentration of sulfur in an aqueous sample including an oxidizable sulfur-containing compound, the process comprising the steps of:

feeding the aqueous sample into an electrolytic cell comprising a reference electrode and an indicator electrode coated with a macrocyclic compound;
  feeding an oxidant into the electrolytic cell;
  allowing the oxidizable sulfur-containing compound to equilibrate with the macrocyclic compound to produce a potential; and
  measuring the potential. Preferably, the process further comprises correlating the measured potential to the concentration of sulfur in the aqueous sample.

In another of its aspects, the present invention provides an apparatus for determining the concentration of sulfur in an aqueous sample comprising:

an electrolytic cell comprising a reference electrode and an indicator electrode coated with a macrocyclic compound;

an inlet to permit entry of the aqueous sample into the electrolytic cell;

an inlet to permit entry of an oxidant into the electrolytic cell; and means for measurement of potential across the indicator electrode and the reference electrode.

In yet another of its aspects, the present invention provides a process for manufacturing a sulfur determination electrode comprising the steps of:

providing a substrate capable of conducting electricity; and applying a coating of a macrocyclic compound to the surface of the substrate.

In yet another of its aspects, the present invention provides a sulfur determination electrode comprising a substrate capable of conducting electricity, the substrate being coated with a macrocyclic compound.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Figure 1:
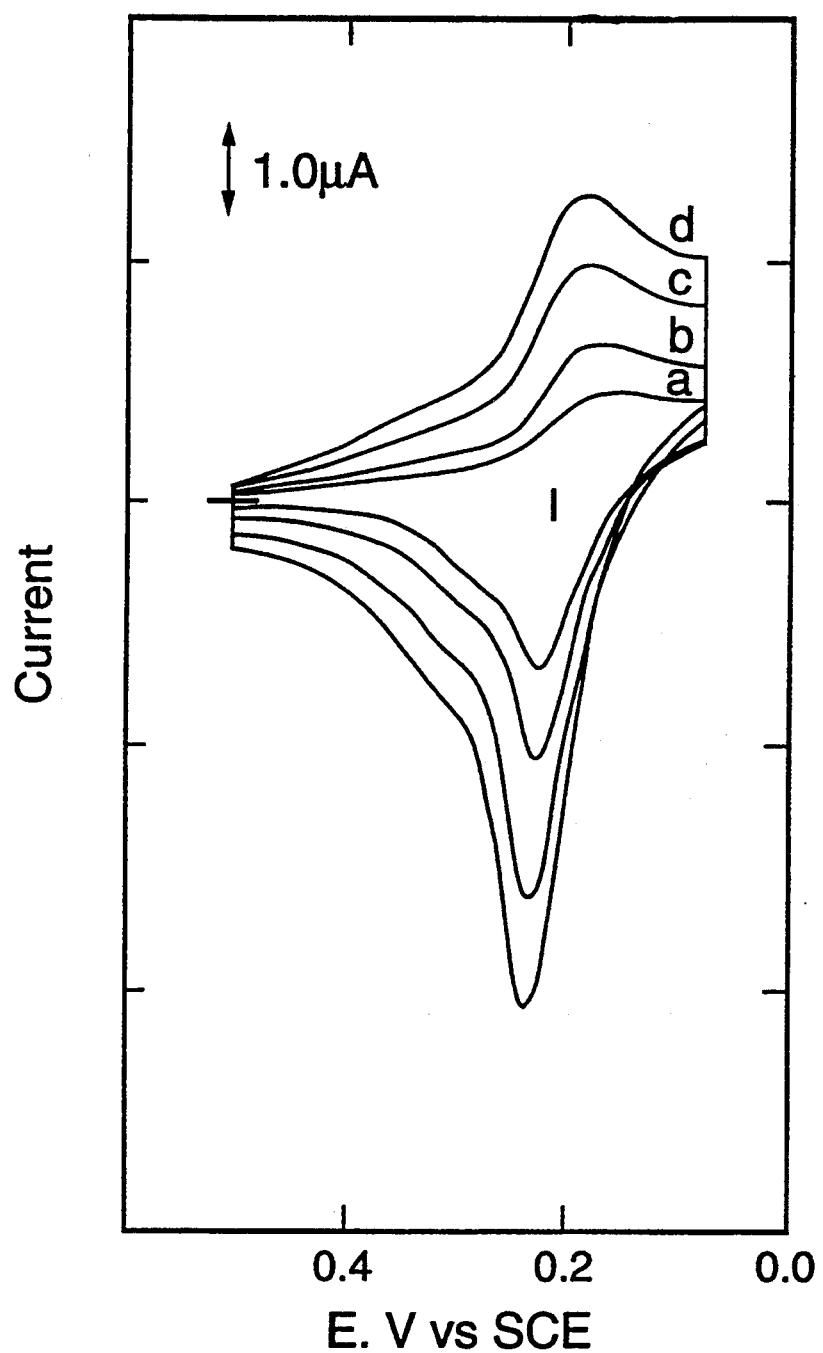
FIG. 1 is a cyclic voltammogram of cobalt(II)N-$N^IN^{II}N^{III}$-tetramethyl-tetra-3,4-pyridinoporphyrazinate (Co(Tmtppa)) in the potential range of from 0 to 500 mV.

The present invention, in various of its aspects, relates to the determination of sulfur in an aqueous sample including an oxidizable sulfur-containing compound. The nature of the compound is not specifically restricted provided that it contain sulfur in an oxidizable form. Thus, while it is envisaged that the invention is useful in the analysis of compounds such as sulfide ion (e.g. $HS^-$, $S^{2-}$ and the like) which are difficult to analyze, the invention is expected to have more widespread utility to other compounds containing oxidizable sulfur, such as mercaptans (RSH).

As used throughout this specification, the term "indicator electrode" is meant to encompass an electrode whose operation during the present process is indicative of the composition of the aqueous sample in which it is immersed. In contrast, as used throughout this specification the term "reference electrode" is an electrode whose operation during the present process is relatively unaffected by the composition of the aqueous sample in which it is immersed.

Various aspects of the present invention relate to the use of an indicator electrode coated with a macrocyclic compound. In this context, the term "macrocyclic compound", when used throughout the present specification (i.e. when coated on a electrode), is meant to encompass an organic macrocyclic compound containing a metal therein. Generally, the macrocyclic compound should meet two requirements:

1. It should be capable of participating in the oxidation of oxidizable sulfur contained in the aqueous sample thereby becoming reduced itself; and
2. The so reduced macrocyclic compound should be oxidizable so that the electrode coated with the macrocycle can be cycled between oxidized and reduced forms.

The particular choice of macrocyclic compound is not restricted provided that it can meet the foregoing two requirements. Preferably, the macrocyclic compound is selected from the group comprising metal phthalocyanines, metal porphyrazines and metal azaporphyrins.

Metal phthalocyanines, such as cobalt and iron complexes, are useful for coating the indicator electrode. Non-limiting examples of derivatives of phthalocyanine useful for coating the indicator electrode include tetraneopentoxyphthalocyanine and tetraaminophthalocyanine.

Phthalocyanines are discussed in an article authored by one of the present inventors and entitled "THE OTHER PERIODIC CHART", Chemtech, August 1987, 506–510 [Lever], the contents of which are hereby incorporated by reference.

Generally, the building block of a phthalocyanine has been shown to be a mono-nuclear structure comprising a square planar unit about a central metal atom:

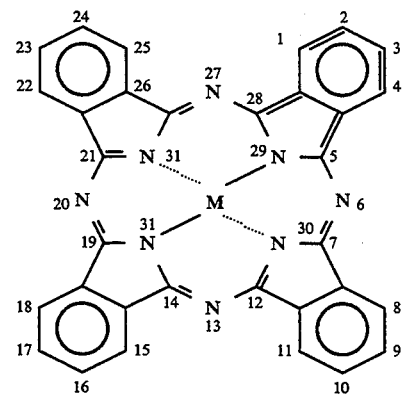

For present purposes the preferred metal atoms are iron and cobalt, although manganese may also be used in certain instances. Iron and cobalt are preferred because of their favourable redox potentials. The more preferred metal is cobalt which has been found, to date, to provide superior experimental results.

Polynuclear analogs of the square planar unit are also useful in the present invention. Specifically, binuclear and tetranuclear analogs are useful in certain cases. An example of a tetranuclear metal phthalocyanine useful in the present invention is a multi-nuclear cobalt phthalocyanine generally represented by the following structural formula:

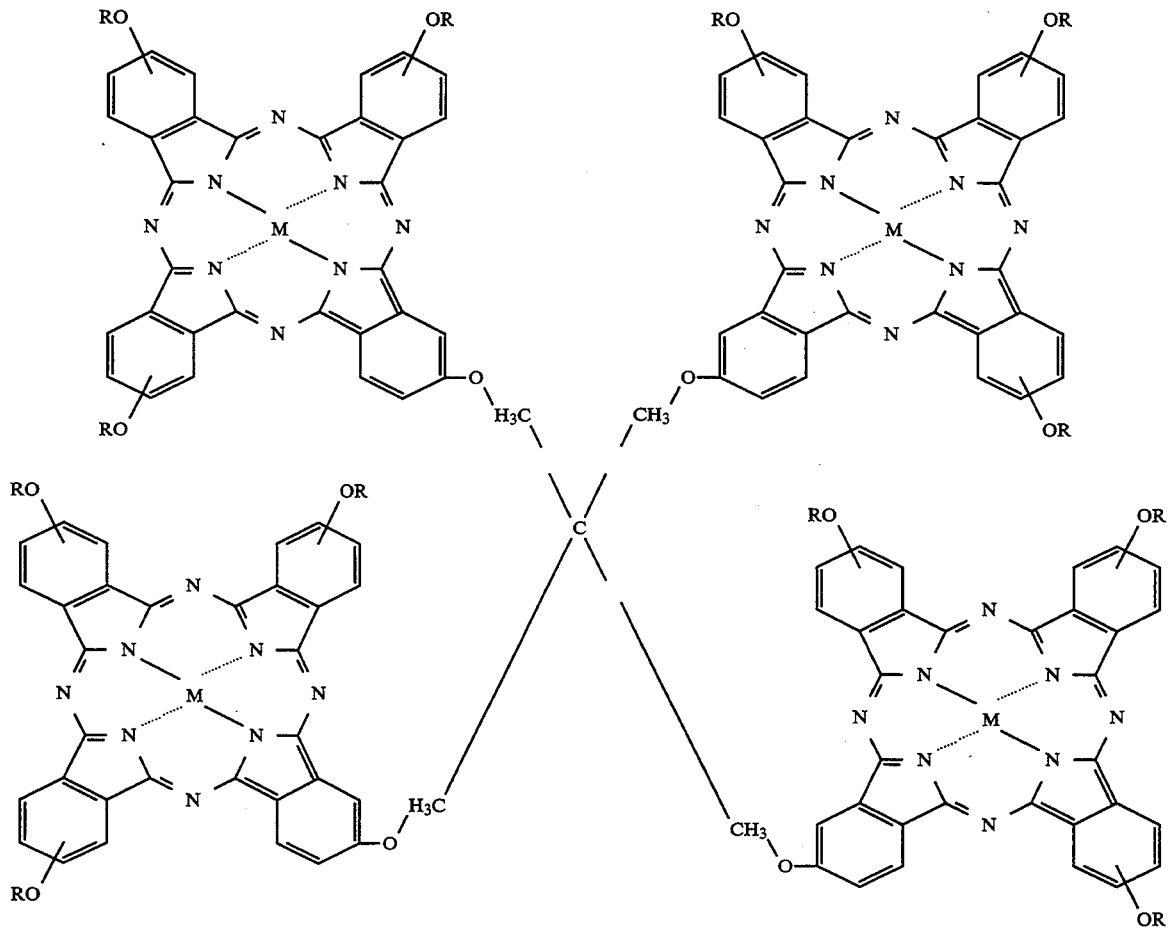

wherein M is cobalt.

The foregoing discussion of phthalocyanines applies equally to metal porphyrazines and metal azaporphyrins.

As described hereinabove, the indicator electrode for use in the present invention is one which is coated with a macrocyclic compound. Generally, this coating will be applied over a substrate made of a conventional electrode material. Non-limiting examples of a suitable substrate include graphite, stainless steel, platinum and the like. Base metals may also form a suitable electrode to be coated; however, base metal electrodes are most suitable for use when the coating applied thereon forms a thick layer. Preferably, the phthalocyanine coating is applied to the electrode as a thin layer or monolayer. The preferred substrate for forming an indicator electrode is graphite, such as stressed annealed pyrolytic graphite (SAPG, also known as highly oriented pyrolytic graphite (HOPG)) and ordinary pyrolytic graphite (OPG). SAPG is more preferred since it provides superior accuracy and ease of cleaning compared to OPG.

Further as disclosed hereinabove, the method of manufacturing the sulfide ion determination (indicator) electrode forms an aspect of the present invention. There are several suitable methods by which a macrocyclic compound coating may be applied to the indicator electrode.

In a preferred embodiment of the invention, this electrode is prepared by deposition of a macrocyclic compound film onto the surface of a graphite (preferably SAPG) electrode. Deposition of the macrocyclic compound film may be effected either by physical adsorption of the film onto the electrode or, alternatively, the film may be electrodeposited onto the electrode. The electrochemical reduction of a macrocyclic compound such as cobalt porphyrazine results in the deposition of a cobalt phthalocyanine film onto the electrode surface. The thickness of the cobalt phthalocyanine coating on the electrode may be varied by the time of the electrodeposition and current used to effect the electrodeposition.

Another embodiment of the invention includes coating the electrode with a macrocyclic compound film by evaporation from solvent. This method is also referred to as spin-coating. A solution comprising the macrocyclic compound is sprayed onto a spinning electrode. Spinning of the electrode is maintained after spraying has been terminated and the solvent evaporates off the electrode resulting in a layer of phthalocyanine remaining as a coating on the electrode. The thickness of the coating on the electrode depends on the concentration of macrocyclic compound in the solution, and also varies with the spin rate of the electrode during the coating process.

Further, a Langmuir-Blodgett trough may be used to prepare an indicator electrode having a monolayer coating of the macrocyclic compound.

In a preferred aspect of the invention, the coated indicator electrode may be further coated with a protective film. The film functions to protect the indicator electrode from degradation by sulfur in the sample and reference solutions. Generally, the protection may be conferred by providing a selectively permeable film which inhibits permeation of compounds which could foul the electrode. Accordingly, the protective film may increase the lifetime of the indicator electrode. One example of a suitable protective film for use in coating the indicator electrode is Nafion film, the basic component of which is available from Aldrich.

As is well known in the art of electrolysis, the inability to measure absolute potentials for half-cell processes has been overcome by measuring relative half-cell potentials against a reproducible reference half-cell which utilizes a reference electrode. Indeed, in many electroanalytical techniques, it is highly desirable that the half-cell potential of one electrode be known, constant and completely insensitive to the composition of the solution being analyzed—this is the reference electrode. The reference electrode should (i) be convenient to use, (ii) be easy to assemble and (iii) maintain an substantially constant and reproducible potential in the presence of small currents.

Reference electrodes are known in the art and the particular choice for use in the present invention is not particularly restricted. It will be appreciated by those skilled in the art that the reference electrode should of course be able to withstand the presence of the sulphide ion being measured. A preferred reference electrode is the calomel electrode (CE), whose half-cell may be represented as follows:

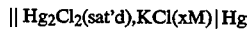

$$\| Hg_2Cl_2(sat'd), KCl(xM) | Hg$$

where x is the molar concentration of potassium chloride in the solution.

A preferred reference electrode for use with the present invention is the saturated calomel electrode (SCE).

Other commercially available reference electrodes are described in R. D. Caton, Jr., J. Chem. Educ., 50, A571 (1973); 51 A7 (1974). Included among these reference electrodes are normal hydrogen electrodes, standard hydrogen electrodes, silver chloride/silver electrodes and mercury sulphate/mercury electrodes.

In the process of the present invention, the aqueous sample is fed into an electrolytic cell comprising a reference electrode and an indicator electrode, coated with a macrocyclic compound film.

An oxidant is also fed into the electrolytic cell. The choice of oxidant is not particularly restricted, however it is preferred to use oxygen due to its abundance and ease of introduction into the electrolytic cell. It will be appreciated that, if the oxidant is oxygen, it may be introduced into the electrolytic cell in a number of suitable ways. For example, the sample may contain sufficient amounts of oxygen resulting in no need for additional oxygen from an external source and thus, it will be understood that, in certain cases, the oxidant may be inherent in the aqueous sample to be analyzed. Alternatively, the aqueous sample may be aerated or bubbled with oxygen prior to analysis. The point here is that the manner by which the oxidant is introduced to the electrolytic cell is not critical provided that the oxidant be available to interact with the reduced macrocycle on electrode substrate. Generally, it is preferred to have a substantially constant concentration of oxidant in the electrolytic cell.

The interaction between the reduced macrocycle and oxidant in the electrolytic cell containing the present indicator electrode results in the production of a potential from a spontaneous equilibrium reaction occurring within the cell.

Generally, it is preferred to maintain the pH of the aqueous sample in the electrolytic cell in the range of from about 6 to about 13. This can be conveniently accomplished by adding a buffer to the aqueous sample. The preferred buffer for use is a mixture comprising a weak acid and the salt the weak acid itself. A non-limiting and preferred example of such a buffer is a mixture comprising sodium phosphate and sodium hydrogen phosphate. The buffer functions to stabilize the pH of the system in order to avoid inaccuracies in the sulfur determination that may be caused by fluctuations in pH.

Similarly, will not required, in some cases, it may be desirable to added an electrolyte to the aqueous sample. Of course it will assist in determination of the sulfide ion in the aqueous sample if the added electrolyte (if used) is free from sulfur. The electrolyte may be added in any suitable form. For example, if the electrolyte is a solid, it may be dissolved in the aqueous sample to be used prior to entry into or while actually in the electrolytic cell. Alternatively, the electrolyte may be dissolved and stored as a solution in a separate vessel. The electrolyte solution would then be added, as required to the electrolytic cell. If the electrolyte is in the form of a liquid, it may be added, as required, to the electrolytic cell either neat or in the form of a dilute aqueous solution. The electrolyte functions to establish a circuit between the reference and indicator electrodes which results in a potential across the two electrodes.

It will be appreciated that certain buffer systems can also serve the purpose of an electrolyte, and thus, when used, the buffer and electrolyte may be the same compound or mixture of compounds.

As described hereinabove, the sulfide determination (indicator) electrode may be conveniently used to conduct direct potentiometric measurements for the analysis of sulfide ion in an aqueous sample. Indeed, in the present process for determining the concentration of sulfur, the potential arising across the reference and indicator electrodes is correlated to the concentration of sulfur in the aqueous sample. Preferably, this involves comparing the potential developed by the indicator electrode in the aqueous sample with its potential when immersed in a standard solution of the analyte. This type of direct potentiometric measurement is readily adaptable to the continuous and automatic monitoring of sulfur concentration.

A convenient way of effecting direct potentiometric measurements is to utilize an empirical calibration curve which is a plot of electrode potential (y) versus log [standard sulfide solution] (x). In this instance the standard sulfide solution may be prepared from any suitable sulfide source. A non-limiting example of such a sulfide is sodium sulfide. The concentration of sulfide ion in a test aqueous sample may then be determined by measuring the electrode potential (indicator electrode vs. reference electrode) and correlating this to the corresponding sulfide concentration on the calibration curve. In the case where the phthalocyanine-coated electrode system has been found to be stable and reproducible from one determination to the next, a calibration of the phthalocyanine-coated electrode is not required prior to use and previously generated standard values may be referred to in determining sulfur ion concentration.

While it is not intended to limit the present invention by any particular theory or mode of action, it is believed that the redox reaction occurring in the electrolytic cell is oxidation of oxidizable sulfur present in the aqueous sample to form elemental sulfur and reduction of oxygen in the aqueous sample to form peroxide. In the case where the macrocyclic coating is cobalt (II) phthalocyanine and the aqueous sample is buffer solution including sulfide ion in the form of $HS^-$ (or $S^{2-}$ or an equilibrium mixture of $HS^-/S^{2-}$), it is believed that the half-reactions involved are (Pc≡phthalocyanine):

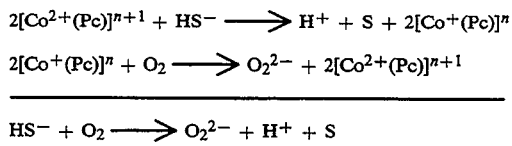

$$2[Co^{2+}(Pc)]^{n+1} + HS^- \longrightarrow H^+ + S + 2[Co^+(Pc)]^n$$

$$2[Co^+(Pc)]^n + O_2 \longrightarrow O_2^{2-} + 2[Co^{2+}(Pc)]^{n+1}$$

$$HS^- + O_2 \longrightarrow O_2^{2-} + H^+ + S$$

The indicator electrode may be used to determine the concentration of sulfur in an aqueous sample. The source of the aqueous sample is not particularly restricted. It is envisaged that source of the aqueous sample could be effluent from pulp and paper plants or from oil and gas refineries. For example, there are approximately 1200 small oil wells in Western Canada and the United States which use ethanolamine strippers to control $H_2S$ emissions. For proper maintenance and control measures, it is necessary to analyze effluent from these ethanolamine baths for sulfide content on a regular, typically daily or even more frequent, basis. Using the present invention, this type of analysis may be conducted rapidly, efficiently and in an on-line fashion.

Embodiments of the present invention will now be illustrated by the following non-limiting specific examples:

EXAMPLE 1

Preparation of Cobalt Tetrapyridinoporphyrazine: Co(Tmtppa)

Cobalt(II)tetra-3,4-pyridinoporphyrazinate (Co(Tppa)) was synthesized according to the standard methods of preparation of phthalocyanines described by Richoux et al. in *Inorganic Chim. Acta*, 1986, 118:115. Specifically, urea, cobalt chloride and 3,4-pyridine dicarboxylic acid, each being of reagent-grade quality, were heated under reflux for 20 hours in nitrobenzene using ammonium molybdate as a catalyst. The crude product was washed with diluted solutions of NaOH and HCl in water, respectively, and further purified by extraction with acetone and water.

Co(Tmtppa) was prepared by alkylation of Co(Tppa) with dimethyl sulphate in DMF according to the procedure outlined by Smith et al., *Chem. Soc. Dalton Trans.*, 1983, p. 1391. The product was recrystallized twice from water and acetone. The product is a mixture of isomers with porphyrazine pyridine rings in the 3 and 4 positions.

Figure 2:
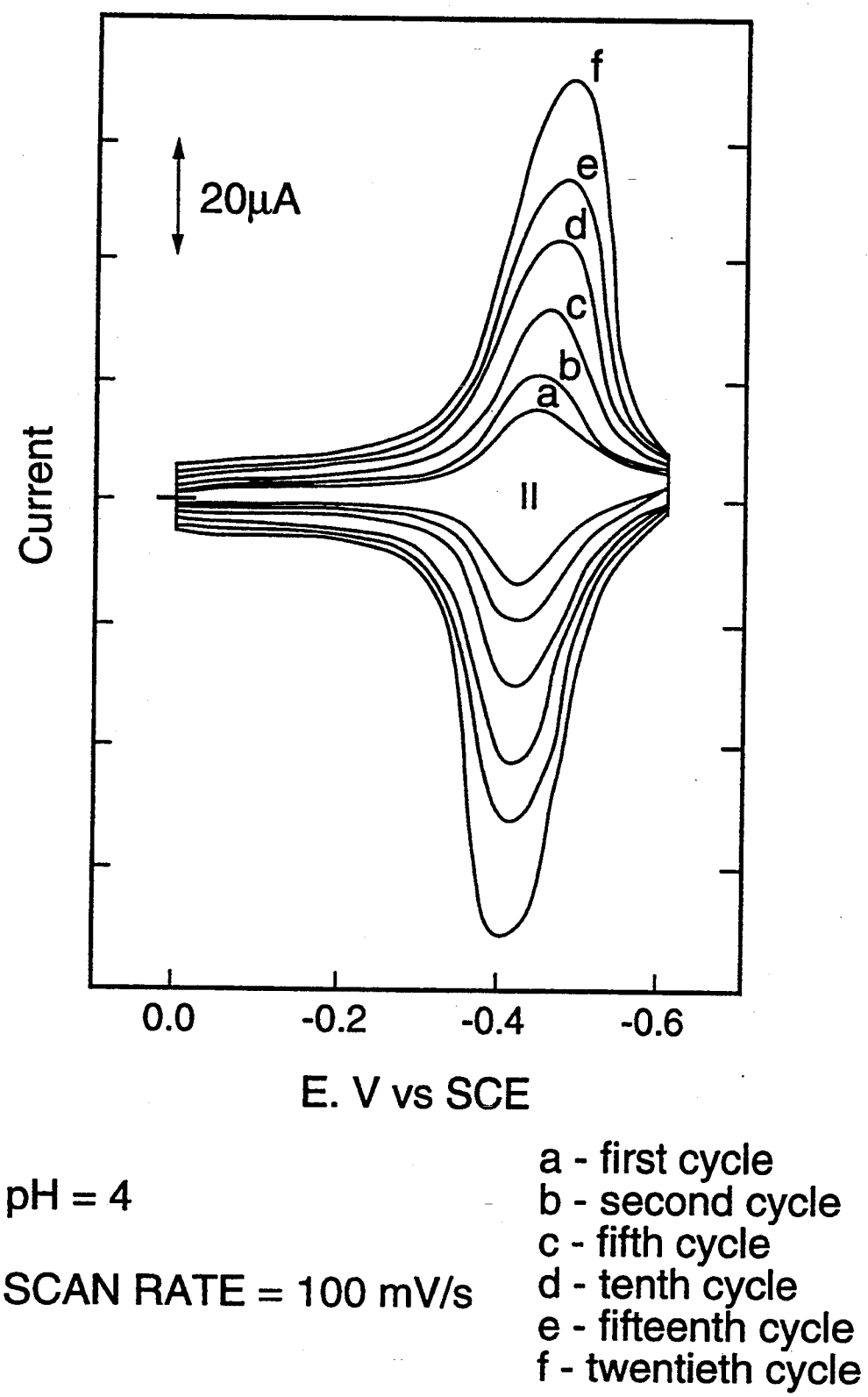
FIG. 2 is a cyclic voltammogram of Co(Tmtppa) in the potential range of from 0 to $-600$ mV.

Cyclic voltammetry (CV), using a Pine Instrument RDE-3 potentiostat and Pine Instrument PIR rotator, of a solution of Co(Tmtppa) in 0.1M phosphate buffer, pH 4, deoxygenated by argon, was performed in the potential range of from 0 to 500 mV and from 0 to −600 mV. The potential was recorded with a Fluke 75 digital multimeter. A peak couple (I) at 250 mV and a peak couple (II) at −440 mV resulted as shown in FIGS. 1 and 2, respectively.

Repeated scanning in the potential range from 0 V to −600 mV resulted in an increase of the peak current of peak couple (II) assigned to the porphyrazine ligand redox reaction. The increase of the peak current indicated formation of a conductive porphyrazine film by electrodeposition. A purple film was observed on the electrode surface.

Cyclic voltammetry conducted in the potential range of from 0 to 500 mV yielded peak couple (I) having a peak to peak separation of 40 mV and asymmetry of oxidation and reduction peak. Surface oxidation of the reduced form was indicated by a sharp, narrow anodic peak and by linear dependence of the peak current on the scan rate. The peak current of a broader cathodic peak appeared to be a linear function of $v^{\frac{1}{2}}$ indicating that the electrochemical reduction is controlled by diffusion of the oxidized form.

Figure 3:
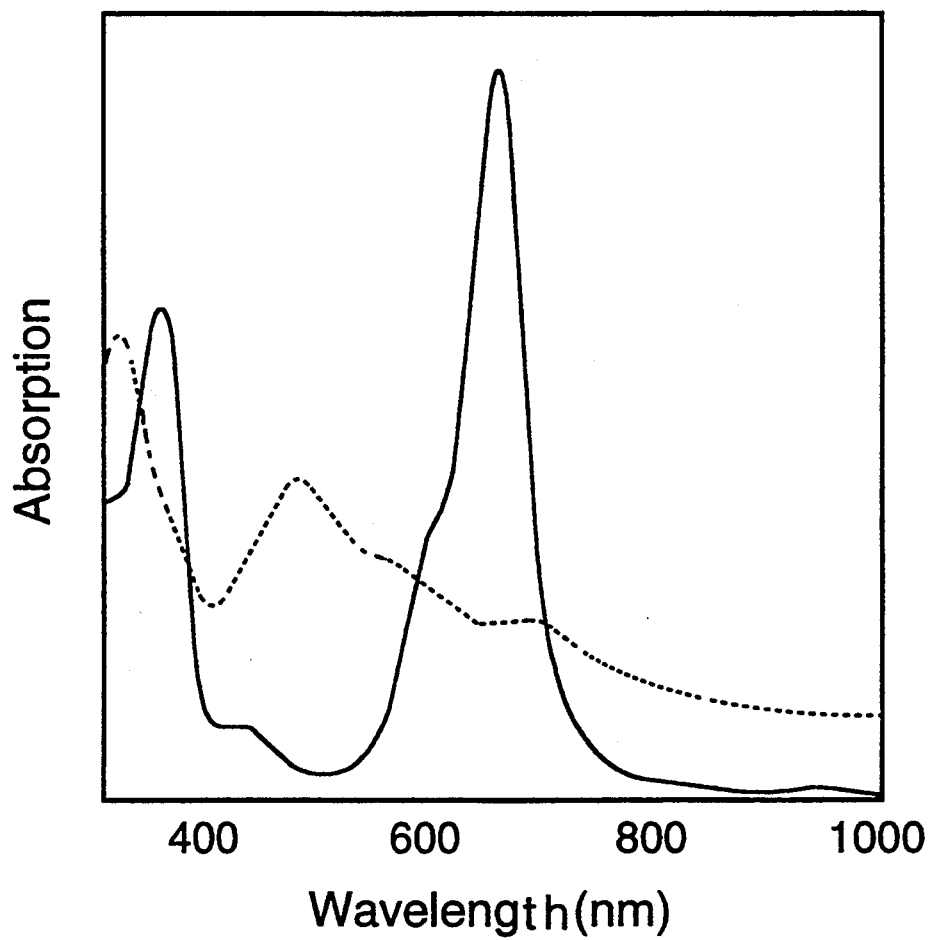
FIG. 3 illustrates the absorption spectra of a solution of Co(Tmtppa) in phosphate buffer (solid line) and its reduced form deposited on a transparent $SnO_2$ electrode.

The absorption electronic spectra, obtained using a Cary Model 2400 spectrometer, of Co(Tmtppa) and its reduced form, which was prepared by electrochemical reduction at 0 V on an optically transparent $SnO_2$ electrode, are shown in FIG. 3.

A strong ESR signal, obtained using a Varian E4 spectrometer, was recorded for Co(Tmtppa). The reduced form was found to be ESR silent.

Preparation Of Co(Tmtppa)-Coated Electrode

The electrodeposition of Co(Tmtppa) was performed by polarization of a highly oriented pyrolytic graphite (HOPG) electrode in the range of from 0 to −600 mV for 5 minutes in a solution of Co(Tmtppa), $10^{-4}$M, in phosphate buffer of pH 4, deoxygenated by argon. The electrode was rinsed with water, vacuum-dried and covered by a Nafion film to protect the electrodeposited film of reduced Co(Tmtppa). The Nafion film was prepared by evaporation of Nafion solution (Aldrich, 5% wt Nafion solution) diluted 50 times by butan-1-ol (BDH). The coated electrode was kept in vacuum for 1 hour to remove completely the solvent.

Figure 4:
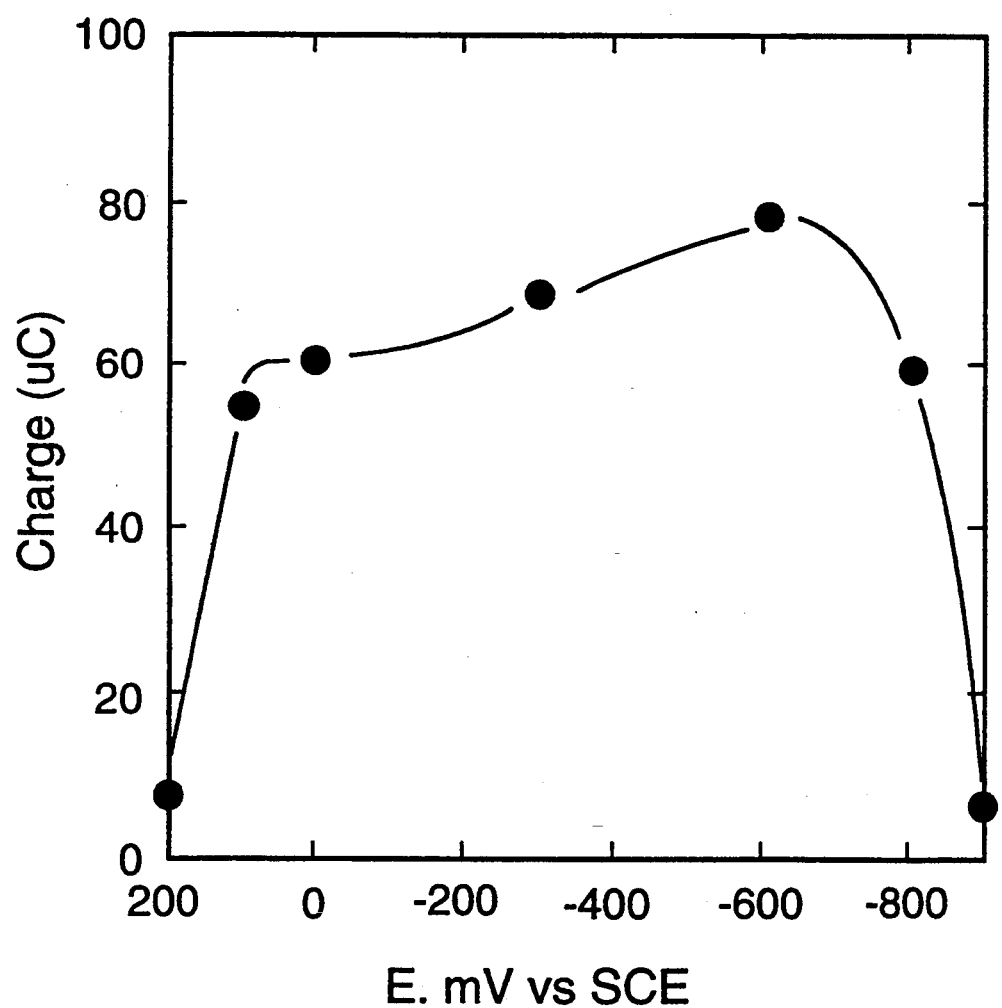
FIG. 4 is a plot of the charge under the cathodic peak of FIG. 2 versus the polarization potentials.

The electrochemical deposition was performed by polarizing the electrode negative to the potential of the redox couple (I). The optimum potential range for electrodeposition was determined by measuring the charge corresponding to the anodic peak of couple (II) after polarizing the electrode at different potentials for a constant period of time. The rate of electrodeposition is independent of potential in the range of 100 mV to −800 mV, as illustrated in FIG. 4, and is limited only by the diffusion process in the solution. Decrease in the rate of deposition on the positive and negative side of the potential range occurred apparently due to electrochemical oxidation of the deposit and evolution of hydrogen causing the deposit to fall off the electrode.

The porphyrazine-coated electrode was rinsed with water and transferred to fresh phosphate buffer, deoxygenated by argon. Cyclic voltammetry was conducted in the potential range of from 0 to −600 mV. A curve identical to that shown in the scan of the Co(Tmtppa) solution resulted. Linear dependence of the peak current on the scan rate and a peak to peak separation of less than 10 mV independent of scan rate both indicate a rapid surface redox reaction. It was determined that as the thickness of the deposited film increased, the peak to peak separation increased due to the iR drop. It may also be due to the decreasing rate of charge transfer in the deposited layer.

The cyclic voltammetry of the film-coated electrode, conducted in the potential ranges of from 0 to 500 mV and from 0 to −600 mV, did not show any change in the peak current of couple (I) or (II). Scanning positively from the potential of oxidation peak (I), however, did cause a rapid decrease of both couple (I) and (II).

Response of Co(Tmtppa)-Coated Electrode To Sulfide Ion

Before use, the electrode prepared above was soaked in phosphate buffer solution, pH 7, in order to equilibrate the electrode.

Figure 5:
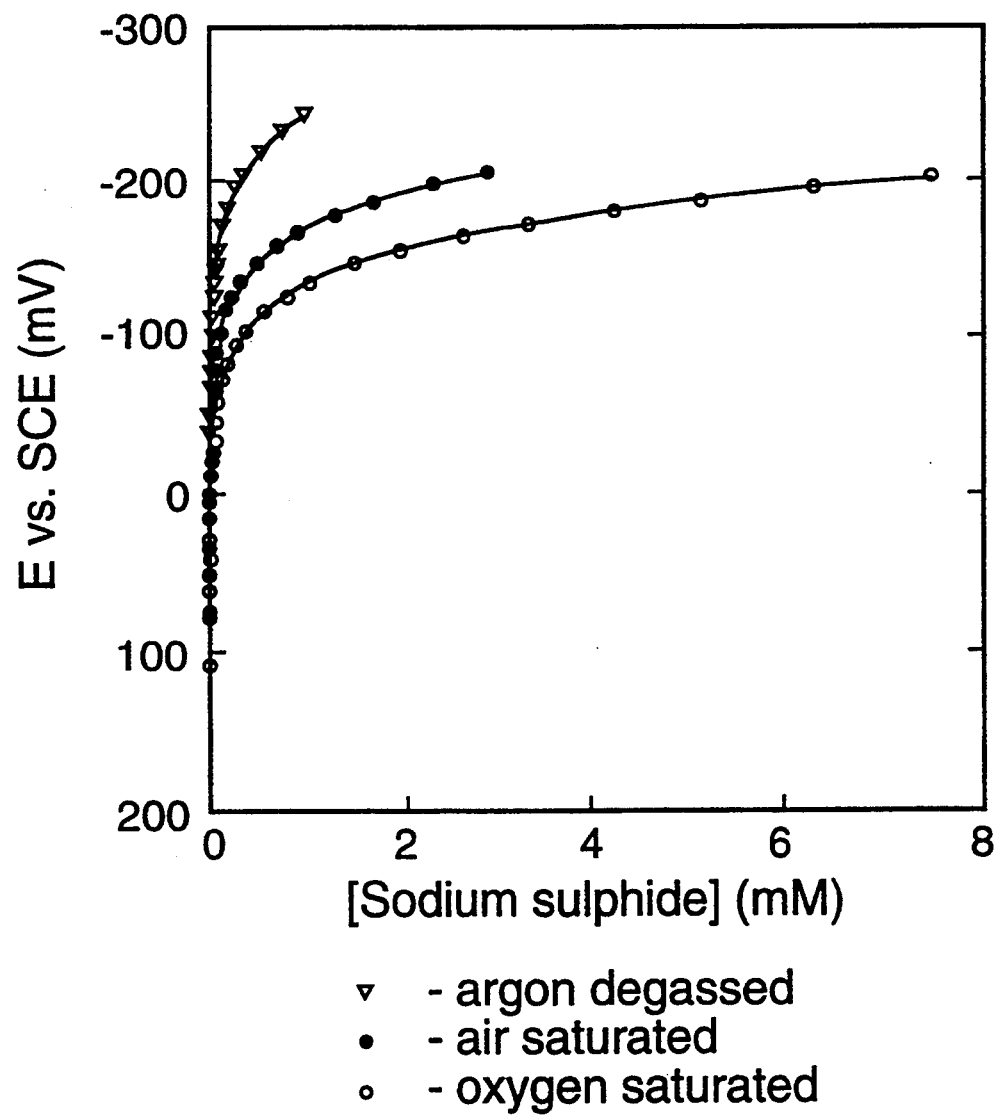
FIG. 5 is a plot of the potential across the electrochemical cell comprising a Co(Tmtppa) electrode/reference electrode versus the concentration of sulfide ion in the buffer solution.
Figure 6:
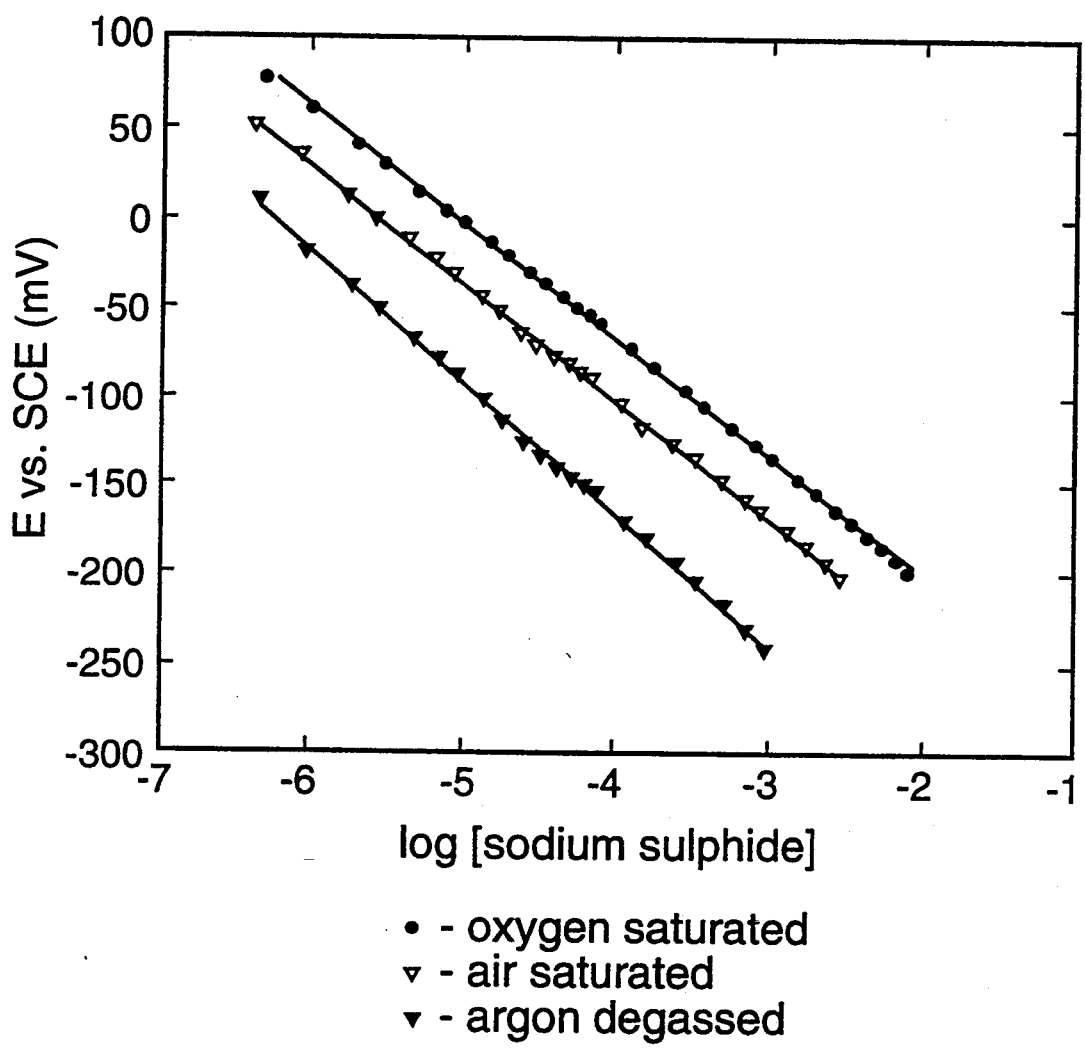
FIG. 6 is a Nernst plot of the results shown in FIG. 5.

Measurements of the concentration of sulfide ion in solution were performed in phosphate buffer, pH 7. Co(Tmtppa) has previously been reported to be unstable at pH>7.5 (Smith et al., J. Chem. Soc. Dalton, 1983, p. 1391), while cobalt tetraminaphthalocyanines have been reported to be stable in a pH range of 7-12.5. The potential of the coated electrode versus a saturated calomel electrode (SCE) was measured at various sulfide concentrations at a constant concentration of oxygen. The results were plotted and are shown in FIG. 5. FIG. 6 illustrates a Nernst plot of the results obtained indicating a linear relationship.

No response was seen for the anions $SO_3^{2-}$, $S_2O_4^{2-}$, $Cl^-$, $Br^-$ and $I^-$ in ranges comparable to the concentrations of sulfide used. Co(Tmtppa) catalyses the decomposition of $S_2O_4^{2-}$ in the presence of oxygen.

Determination Of H2S Concentration In Solution

After each measurement, the Co(Tmtppa) indicator electrode was immersed in 0.1% HCl solution for 15 minutes and then in phosphate buffer, pH 7, until a steady state was established. Aliquots of a standard sodium sulfide solution were added to the phosphate buffer electrolyte and the potential between the indicator and reference electrodes was recorded as follows:

| Volume of Na2S (μl) (0.05 M) | Electrode Potential (mV vs SCE) | |
|---|---|---|
| | Initial | Final |
| 0 | 65 | 65 |
| 1 | −17 | −18 |
| 2 | −30 | −31 |
| 4 | −46 | −46 |
| 6 | −55 | −55 |
| 10 | −70 | −69 |
| 15 | −79 | −78 |
| 20 | −85 | −85 |
| (15 μl unknown added) | −98 | −98 |

The potential across the two electrodes was plotted against the log of the concentration of sodium sulfide.

Figure 7:
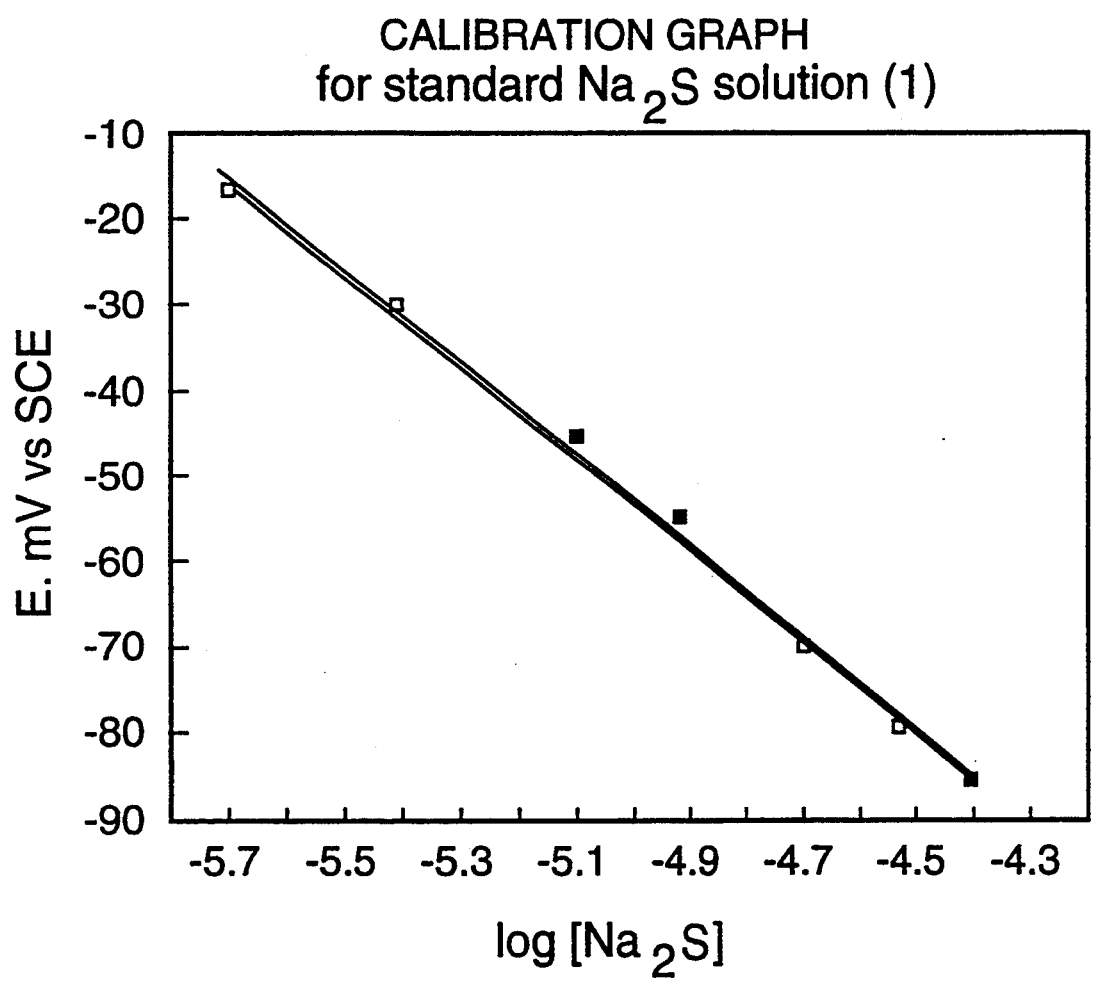
FIG. 7 is a Nernst plot of the results obtained using sodium sulfide standard samples.

The resulting Nernst plot, shown in FIG. 7, was used to determine the concentration of Na2S in an unknown sample (15 μL, $7.5 \times 10^{-7}$ moles). Using this method, the Na2S content was determined to be 16.1 μL±9% ($8.05 \times 10^{-7}$ moles).

EXAMPLE 2

Preparation of Cobalt Tetraaminophthalocyanine: Co(TAPc)

4-Nitrophthalonitrile (3.0 g, 17.3 mmole) was added to 50 ml of dry methanol containing 50 mg of sodium. Ammonia was bubbled into the solution at 80° C. for 3 hours. The solution was then evaporated to provide crude 5-nitro-1,3-diiminoisoindoline.

Anhydrous cobalt (II) chloride (2.8 g, 7.6 mmole) and the crude diiminoisoindoline were mixed in 50 ml of 2-N,N-dimethylaminoethanol and heated up to 160° C. for 20 hours. The crude cobalt tetra-nitrophthalocyanine was obtained after filtration from the hot reaction mixture and subsequent washing with ethanol, water and diluted HCl.

The crude cobalt tetra-nitrophthalocyanine was converted to cobalt tetra-aminophthalocyanine by reaction with sodium sulfide nonahydrate (50 g) in 150 ml water at 50° C. for 5 hours without further purification. The solid product obtained after filtration was washed with dilute HCl and water. The solid was further purified by subjecting it to pre-absorbtion onto flash silica gel and flash chromatography with DMF to yield (45% of theoretical) a green coloured product.

Elemental analysis of the product (Co(TAPc).H2O) yielded the following results: C 60.23; H 3.23; N 24.17 (cf. calculated: C 60.89; H 3.19; N 26.63). An infrared spectrum (KBr disc using Nicolet 20SX Infrared Spectrometer) of the product yielded peaks characteristic of Co(TAPc) (see Achar, B. N.; Fohlen, G. M.; Parker, J. A.; Keshavayya, J Polyhedron, 1989, 6, 1463.) at (cm$^{-1}$): 735, 751, 821, 859, 950, 1059, 1096, 1136, 1254, 1307, 1345, 1384, 1420, 1482, 1497, 1518, 1609, 3182 and 3281. The UV/Visible spectrum of the product (max nm (log(ε))) yielded the following results: 705(4.87), 639(4.47), 412(4.31).

Preparation of Co(TAPc)-Coated Electrode

The electrodeposition of Co(TAPc) was performed by scanning an HOPG electrode in the range of 0 to 1.0 V (vs. Ag/AgCl) in CoTAPc solution using DMF as the solvent under argon degassed conditions. The electrode was then rinsed with ethanol, vacuum-dried and covered by Nafion film to protect the electrodeposited Co(TAPc). The Nafion film was prepared by evaporation on the electrode surface of a solution comprising 1 drop of the commercially available stock solution of Nafion solution (Aldrich, 5% wt Nafion solution) diluted 50 times with butan-1-ol (BDH). The electrode was then kept in a vacuum for 1 hour to remove the solvent substantially completely.

Response Of Co(TAPc)-Coated Electrode to Sulfide Ion

Stock solutions of sodium sulfide were prepared by dissolving reagent grade Na2S.9H2O in water. KIO3 was dried in a vacuum oven at 100° C. for one hour before use. Sodium thiosulphate solution was standardized with KIO3 by the conventional iodometry method. The concentration of the sulfide was determined used excess iodine solution as oxidant which is generated by the oxidation of potassium iodide with standard potassium iodate solution. The excess iodine solution is then back-titrated with thiosulphate solution.

Before the experiment, the electrode was soaked in pH 7 phosphate buffer. During the experiment, 0.1M Na2S solution was injected into the cell with a microliter syringe and the potential of the rotating Co(TAPc)-coated electrode vs. SCE was measured.

Figure 8:
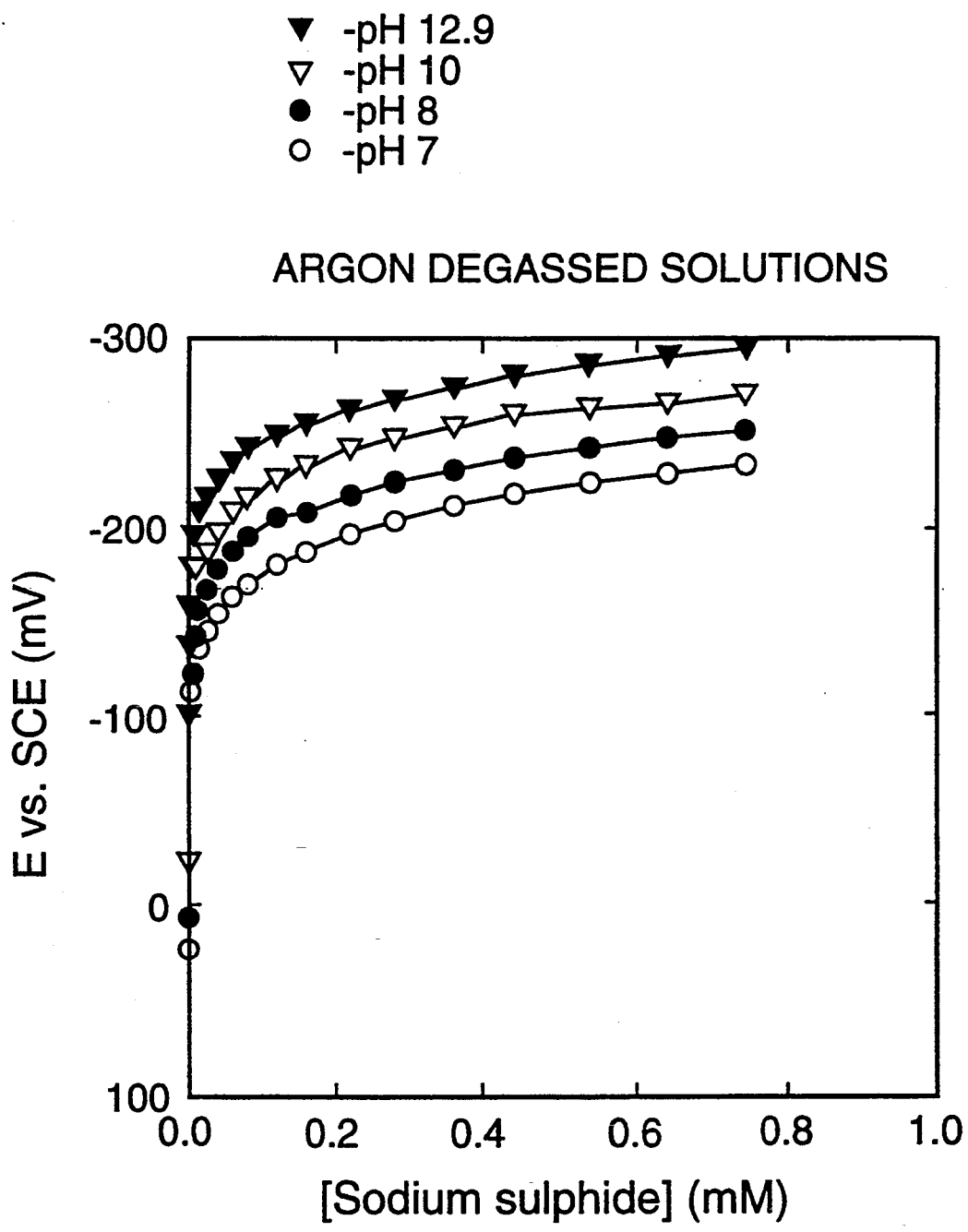
FIGS. 8, 9 and 10 are various plots of potential across the electrochemical cell comprising a cobalt(II)tetraaminophthalocyanine (Co(TAPc)) electrode/reference electrode versus the concentration of sulfide ion in the different buffer conditions and oxygen concentrations.
Figure 9:
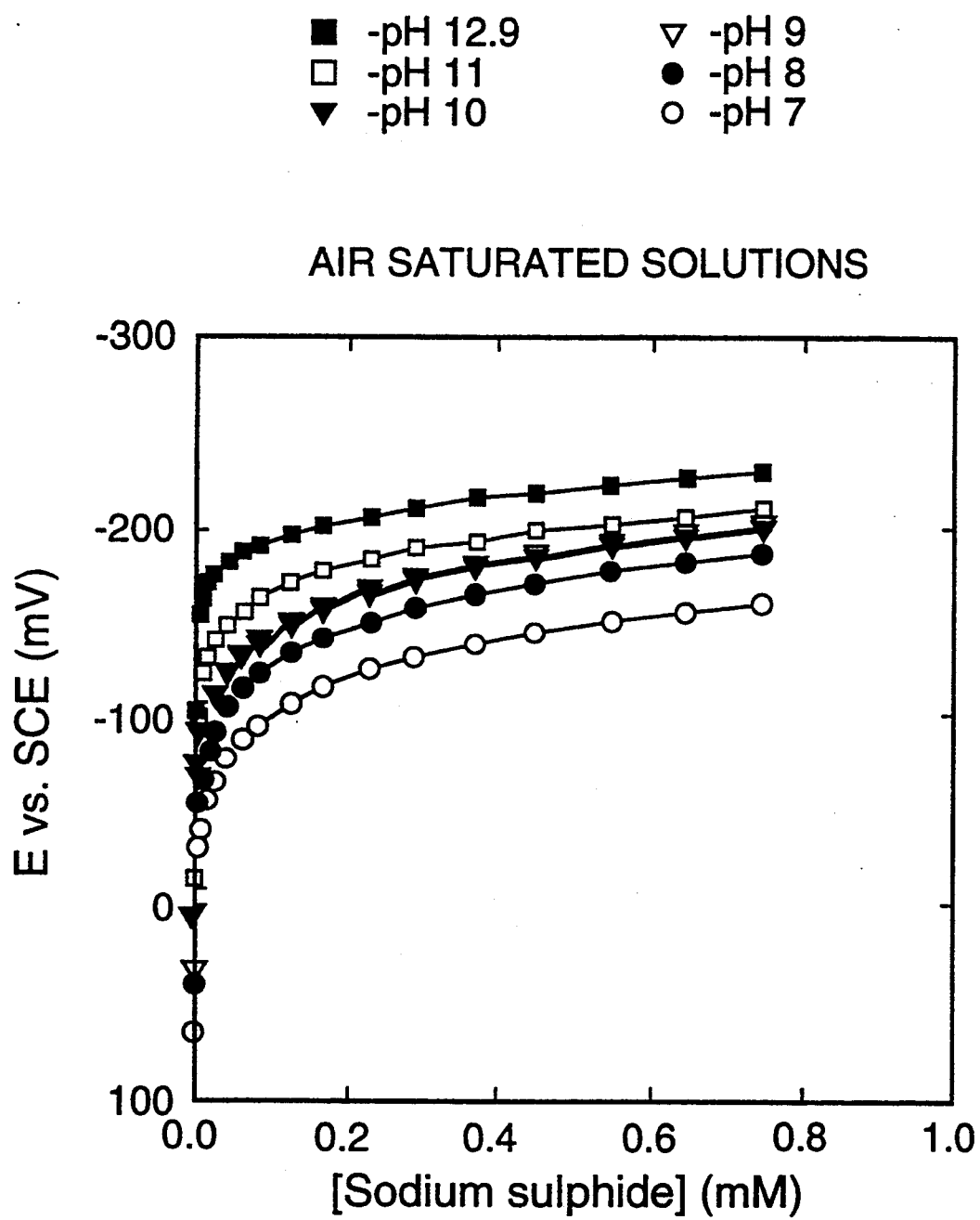
Figure 10:
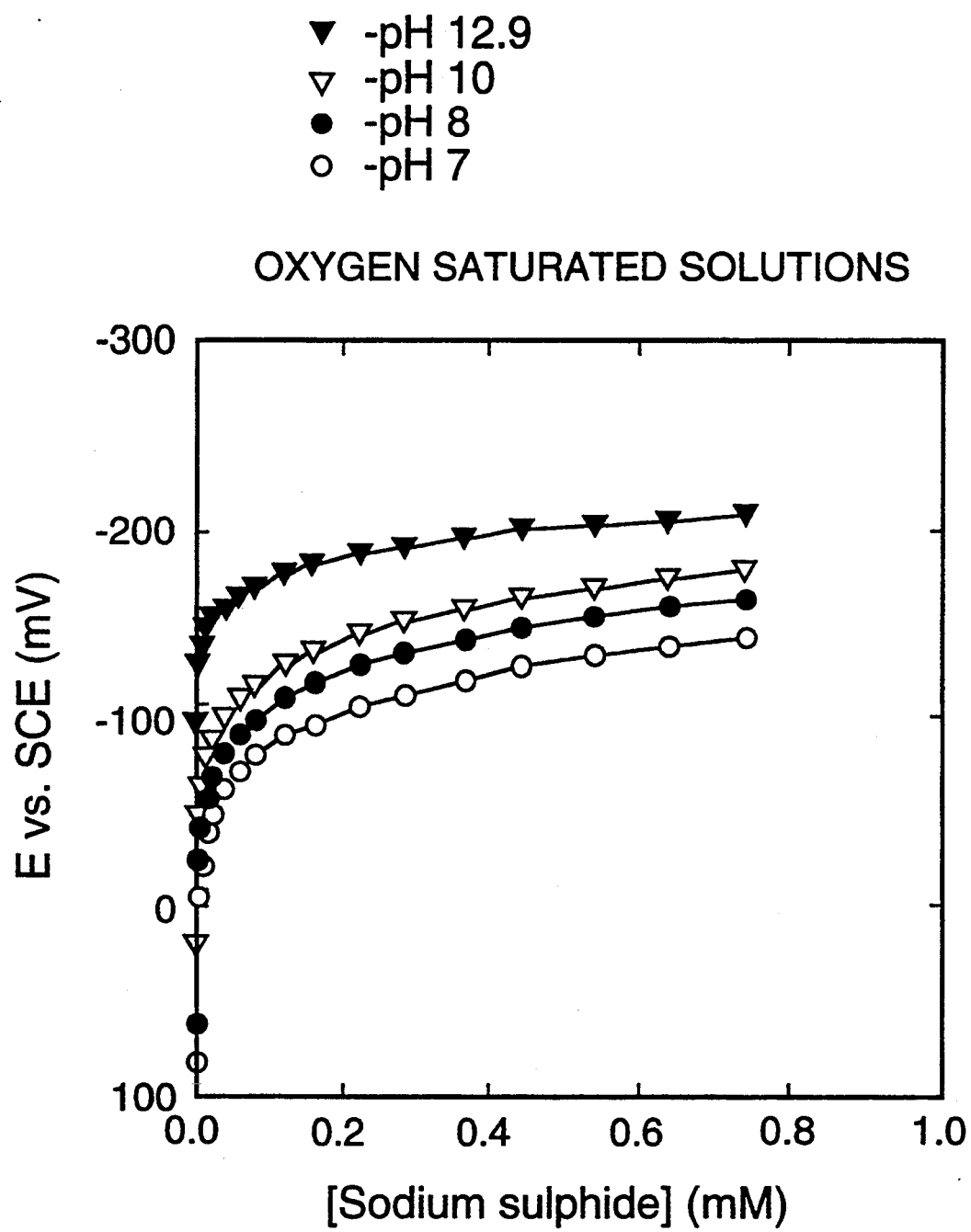
Figure 11:
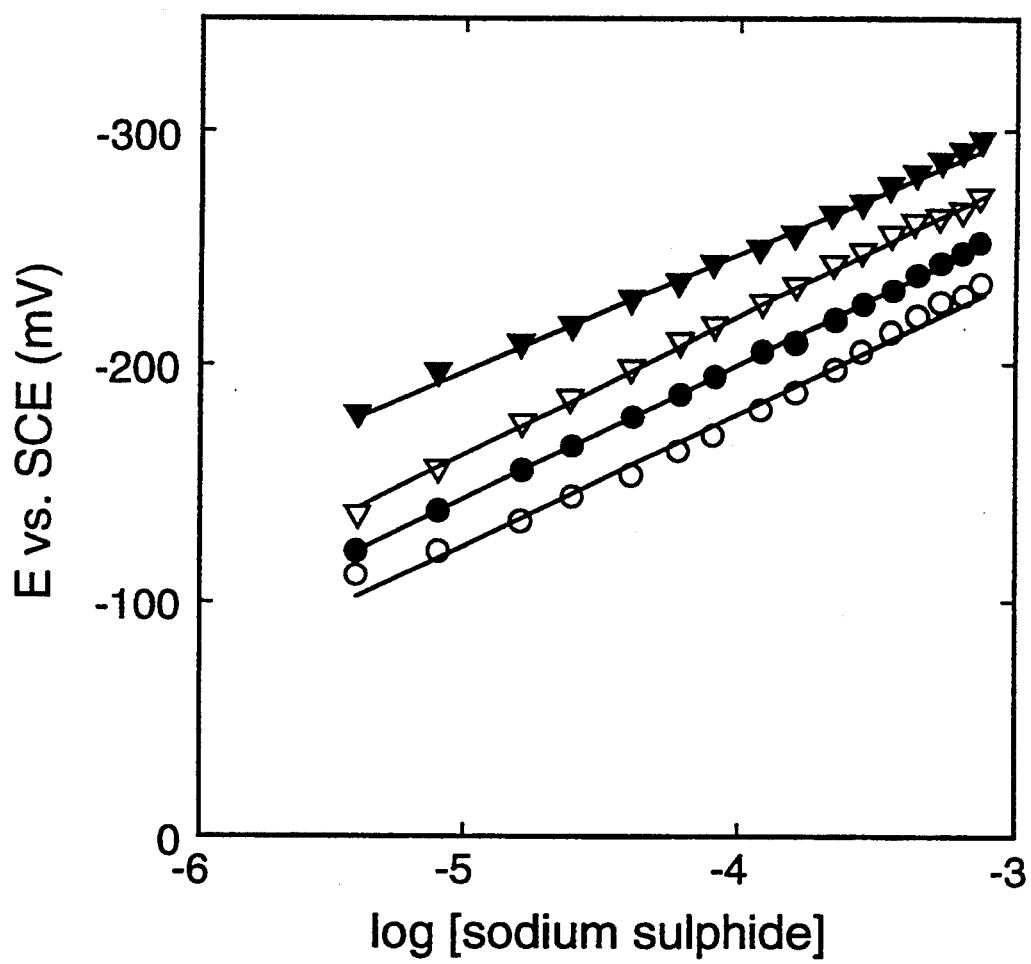
FIGS. 11, 12 and 13 are Nernst plots of the results shown in FIGS. 8, 9 and 10, respectively.
Figure 12:
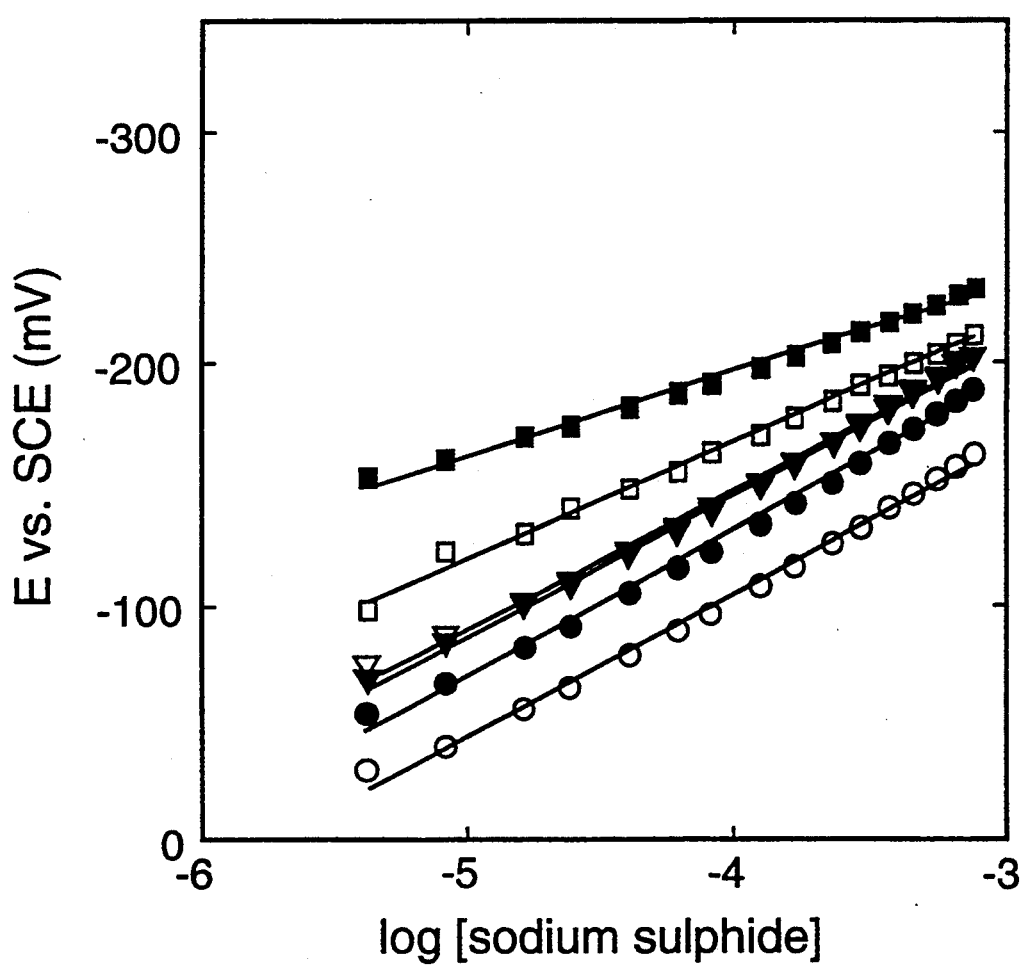
Figure 13:
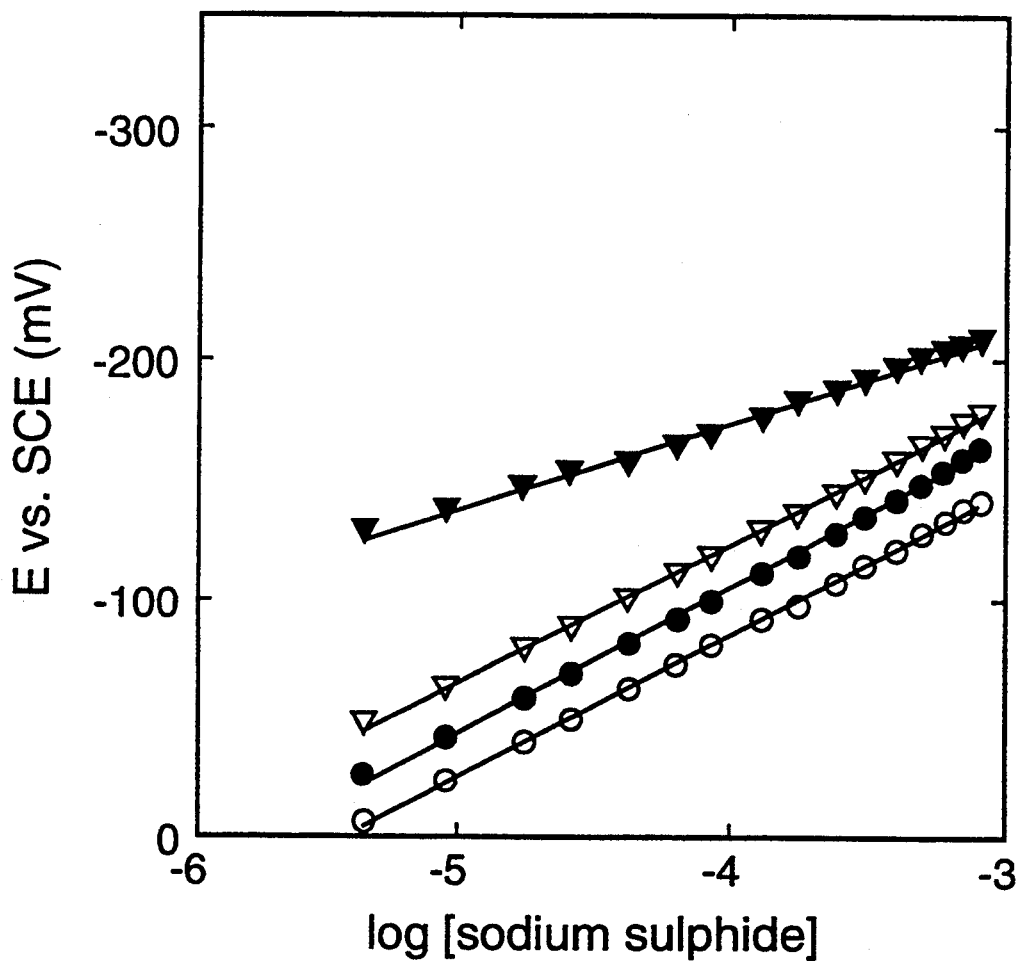

The results of measurement of the Co(TAPc)-coated electrode vs. SCE at varying concentration of sulfide concentration are illustrated in FIGS. 8, 9 and 10 for varying pH and oxygen concentration conditions. The corresponding Nernstian plots are illustrated in FIGS. 11, 12 and 13, respectively, each yielding a straight line.

As is apparent, the dependence of the zero-current potential of the Co(TAPc)-coated electrode on the concentration of sodium sulfide has been found to obey the Nernstian equation for a one-electron redox process when the concentration of oxygen was kept constant at a pH in the range of form 7 to 11.

The Co(TAPc)-coated electrode did not show any response to common ions such as $SO_3^{2-}$, $S_2O_4^{2-}$, $Cl^{31}$, $Br^-$ and $I^-$ and thus the presence of one or more of these ions should not cause any deleterious effect during the measurement of the sulfide ion concentration.

What is claimed is:

1. A process for determining the concentration of sulfur in an aqueous sample including an oxidizable sulfur-containing compound, the process comprising the steps of:
   feeding the aqueous sample into an electrolytic cell comprising a reference electrode and an indicator electrode coated with a macrocyclic compound;
   feeding an oxidant into the electrolytic cell;
   allowing the oxidizable sulfur-containing compound to equilibrate with the macrocyclic compound to produce a potential; and
   measuring the potential.

2. The process defined in claim 1, wherein the macrocyclic compound is a cobalt phthalocyanine.

3. The process defined in claim 1, wherein the macrocyclic compound is a cobalt porphyrazine.

4. The process defined in claim 1, wherein said indicator electrode comprises a protective coating over said macrocyclic compound.

5. The process defined in claim 4, wherein the protective coating consists of a Nafion film.

6. The process defined in claim 1, wherein said reference electrode is a saturated calomel electrode.

7. The process defined in claim 1, wherein said oxidant is oxygen.

8. The process defined in claim 7, wherein the oxygen is inherent in the aqueous sample.

9. The process defined in claim 7, wherein the oxygen is added to the aqueous sample from an external source.

10. The process as defined in claim 9, wherein the oxygen is added by aerating the aqueous sample.

11. The process defined in claim 1, wherein the pH of said aqueous sample is maintained in the range of from about 6 to about 13 by addition of a buffer.

12. The process defined in claim 11, wherein the buffer is a mixture of sodium phosphate and sodium hydrogen phosphate.

13. The process defined in claim 1, wherein the indicator electrode is made of a substrate selected from the group consisting of graphite, stainless steel and platinum.

14. The process defined in claim 1, wherein the indicator electrode is made of a substrate consisting of stressed annealed pyrolyric graphite.

15. The process defined in claim 1, comprising the step of adding an electrolyte to the aqueous sample.

16. The process defined in claim 15, wherein the electrolytic is substantially free of sulfur.

17. A process for determining the concentration of sulfur in an aqueous sample containing an oxidizable sulfur containing compound, the process comprising the steps of:
   feeding the aqueous sample into an electrolytic cell comprising a reference electrode and an indicator electrode coated with a macrocylic compound containing a metal, wherein said macrocyclic compound participates in the oxidation of said sulfur containing compound and is oxidizable so that said indicator electrode may be cycled between an oxidized form and a reduced form;
   feeding an oxidant into the electrolytic cell;
   allowing the oxidizable sulfur compound to equilibrate with the macrocyclic compound to produce a potential; and
   measuring the potential.

18. A process for determining the concentration of sulfur in an aqueous sample containing an oxidizable sulfur containing compound, the process comprising the steps of:
   feeding the aqueous sample into an electrolytic cell comprising a reference electrode and an indicator electrode coated with a macrocylic compound, wherein said macrocyclic compound is selected from the group consisting of metal phthalocyanines, metal porphyrazines and metal azaporphyrins;
   feeding an oxidant into the electrolytic cell;
   allowing the oxidizable sulfur compound to equilibrate with the macrocyclic compound to produce a potential; and
   measuring the potential.

19. The process defined in claim 18, Wherein metal is selected from iron and cobalt.

* * * * *